United States Patent
Jacobs et al.

(10) Patent No.: US 11,957,508 B2
(45) Date of Patent: Apr. 16, 2024

(54) INTRALUMINAL ULTRASOUND SCANNER WITH REDUCED DIAMETER

(71) Applicant: KONINKLIJKE PHILIPS N.V., Eindhoven (NL)

(72) Inventors: Egbertus Reinier Jacobs, Overloon (NL); Johannes Wilhelmus Weekemp, Beek en Donk (NL); Vincent Adrianus Henneken, Utrecht (NL); Marcus Cornelis Louwerse, Nijmegen (NL); Ronald Dekker, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/768,849

(22) PCT Filed: Dec. 10, 2018

(86) PCT No.: PCT/EP2018/084095
§ 371 (c)(1),
(2) Date: Jun. 1, 2020

(87) PCT Pub. No.: WO2019/115424
PCT Pub. Date: Jun. 20, 2019

(65) Prior Publication Data
US 2020/0367854 A1    Nov. 26, 2020

Related U.S. Application Data

(60) Provisional application No. 62/597,563, filed on Dec. 12, 2017.

(51) Int. Cl.
*A61B 8/00* (2006.01)
*A61B 8/12* (2006.01)

(52) U.S. Cl.
CPC .............. *A61B 8/12* (2013.01); *A61B 8/445* (2013.01); *A61B 8/4477* (2013.01);
(Continued)

(58) Field of Classification Search
CPC ....... A61B 8/12; A61B 8/4477; A61B 8/4494; A61B 8/4488; A61B 8/445; A61B 8/0891
See application file for complete search history.

(56) References Cited

U.S. PATENT DOCUMENTS 6,283,921 B1    9/2001   Nix
6,641,540 B2   11/2003   Fleischman
(Continued)

FOREIGN PATENT DOCUMENTS

WO    2017167883 A1    10/2017

OTHER PUBLICATIONS

International Search Report & Written Opinion for PCT/EP2018/084095, dated Feb. 21, 2019.

*Primary Examiner* — Katherine L Fernandez
*Assistant Examiner* — Taylor Deutsch

(57) ABSTRACT

Devices, systems, and methods relating to intraluminal imaging are disclosed. In an embodiment, an intraluminal imaging device is disclosed. One embodiment of the intraluminal imaging device comprises a flexible elongate member configured to be inserted into a body lumen of a patient, the flexible elongate member comprising a proximal portion and a distal portion. The intraluminal imaging device further comprises an ultrasound imaging assembly disposed at the distal portion of the flexible elongate member. The imaging assembly comprises a support member, a flexible substrate positioned around the support member, a plurality of ultrasound transducer elements integrated in the flexible substrate, and a plurality of control circuits disposed on the flexible substrate at a position proximal to the plurality of (Continued)

transducer elements. The plurality of control circuits has an outer profile that does not extend beyond an outer profile of the plurality of transducer elements.

22 Claims, 14 Drawing Sheets

(52) U.S. Cl.
CPC .............. *A61B 8/4494* (2013.01); *A61B 8/54* (2013.01); *A61B 8/4488* (2013.01)

(56) References Cited

U.S. PATENT DOCUMENTS

| | | | |
|---|---|---|---|
| 6,776,763 B2 | 8/2004 | Nix | |
| 7,226,417 B1 | 6/2007 | Eberle | |
| 7,846,101 B2 | 12/2010 | Eberle | |
| 2002/0087083 A1 | 7/2002 | Nix | |
| 2004/0044286 A1 | 3/2004 | Hossack | |
| 2007/0239024 A1* | 10/2007 | Eberle | B06B 1/0633 600/459 |
| 2012/0265192 A1* | 10/2012 | Sliwa | A61B 8/5223 606/33 |
| 2014/0180141 A1* | 6/2014 | Millett | A61B 5/6851 600/486 |
| 2014/0180143 A1* | 6/2014 | Millett | A61B 5/6851 600/488 |
| 2015/0305710 A1 | 10/2015 | Stigall | |
| 2016/0007962 A1* | 1/2016 | Esbeck | A61B 8/12 600/467 |
| 2016/0029999 A1 | 2/2016 | Corl | |

\* cited by examiner

INTRALUMINAL ULTRASOUND SCANNER WITH REDUCED DIAMETER

TECHNICAL FIELD

The present disclosure relates generally to intraluminal imaging and, in particular, to the ultrasound imaging assembly of an intraluminal imaging device. The imaging assembly can include an array of transducers positioned on a flexible substrate that is wrapped circumferentially around a support structure.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state IVUS catheters carry a sensing assembly or scanner assembly that includes an array of ultrasound transducers distributed around its circumference along with one or more integrated circuit controller chips mounted adjacent to the transducer array. The solid-state IVUS catheters are also referred to as phased array IVUS transducers or phased array IVUS devices. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element (as in a rotational IVUS catheter), the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing a solid-state IVUS catheter that has a small diameter to easily traverse tortuous vasculature can be challenging. In some instances, the controller chips and/or the ultrasound transducers can undesirably increase the diameter of the distal end of the catheter. In some instances, interference between the controller chips and/or the ultrasound transducers can undesirably reduce image quality.

SUMMARY

Embodiments of the present disclosure provide improved intraluminal imaging system for generating ultrasound images within a body lumen such as a blood vessel. In that regard, the present disclosure provides for an imaging assembly with an integrated flexible substrate and a support member around which the flexible substrate is wrapped. A flexible interconnect layer is processed onto a prepared transducer array and provided with a plurality of control circuits such that an outer profile of the plurality of control circuits does not extend beyond an outer profile of the transducer array when the flexible substrate is wrapped around the support member. The control circuits may be outside a transmission zone of the transducer array thereby reducing interference with the transmitted ultrasonic signals resulting from their contact with highly reflective control circuits. Accordingly, the disclosed embodiments can improve image resolution and quality.

In one embodiment, an intraluminal imaging device is disclosed. The intraluminal imaging device comprises a flexible elongate member configured to be inserted into a body lumen of a patient, the flexible elongate member comprising a proximal portion and a distal portion. The intraluminal imaging device further comprises an ultrasound imaging assembly disposed at the distal portion of the flexible elongate member. The imaging assembly comprises a support member, a flexible substrate positioned around the support member, a plurality of ultrasound transducer elements integrated in the flexible substrate, the plurality of transducer elements comprising an outer profile, and a plurality of control circuits disposed on the flexible substrate at a position proximal to the plurality of transducer elements, the plurality of control circuits comprising an outer profile that does not extend beyond the outer profile of the plurality of transducer elements.

In some embodiments, the support member comprises a proximal portion and a distal portion, wherein the proximal portion comprises a plurality of recesses each configured to receive a control circuit therein. In some embodiments, the distal portion of the support member comprises a spool configured to receive the plurality of transducer elements. In some embodiments, the plurality of control circuits are longitudinally co-located with the plurality of recesses and the plurality of transducer elements are longitudinally co-located with the spool. In some embodiments, the proximal portion of the support member comprises four recesses. In some embodiments, the flexible substrate comprises a plurality of slits distal to the plurality of control circuits. In some embodiments, the plurality of slits are arranged to permit the plurality of control circuits to be depressed toward the support member. In some embodiments, the flexible substrate includes circuitry enabling lateral communication between control circuits. In some embodiments, the support member is made of at least one of stainless steel or a polymer.

In one embodiment, a method is disclosed. The method comprises providing a flexible substrate having a plurality of ultrasound transducer elements integrated therein, locating a plurality of control circuits on the flexible substrate at a position proximal to the plurality of transducer elements, and positioning the flexible substrate around a support member such that an outer profile of the plurality of control circuits does not extend beyond an outer profile of the plurality of ultrasound transducer elements.

In some embodiments, locating the plurality of control circuits on the flexible substrate comprises locating the plurality of control circuits on a depressible region of the flexible substrate. In some embodiments, the support member comprises a proximal portion and a distal portion wherein the proximal portion includes a plurality of recesses each sized and shaped to receive a control circuit therein. In some embodiments, the support member comprises four recesses. In some embodiments, the flexible substrate comprises a plurality of slits disposed distal to the plurality of control circuits and configured to permit the plurality of control circuits to be depressed into the plurality of recesses. In some embodiments, the method further comprises depressing the plurality of control circuits into the plurality of recesses. In some embodiments, the distal portion of the support member includes a spool sized and shaped to receive the plurality of ultrasound transducer elements. In some embodiments, positioning the flexible substrate around the support member comprises wrapping the plurality of ultrasound transducer elements around the spool. In some embodiments, the flexible substrate includes circuitry enabling lateral communication between control circuits. In some embodiments, the support member is made of at least one of stainless steel or a polymer. In some embodiments, the plurality of ultrasound transducer elements comprises a plurality of capacitive micromachined ultrasound transducers.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 12 is a diagrammatic side view of the exemplary transducers with the flexible substrate in a flat configuration, and FIG. 13 is a diagrammatic side view of the exemplary transducers with the flexible substrate in a curved (or rolled) configuration.

DETAILED DESCRIPTION

Figure 1:
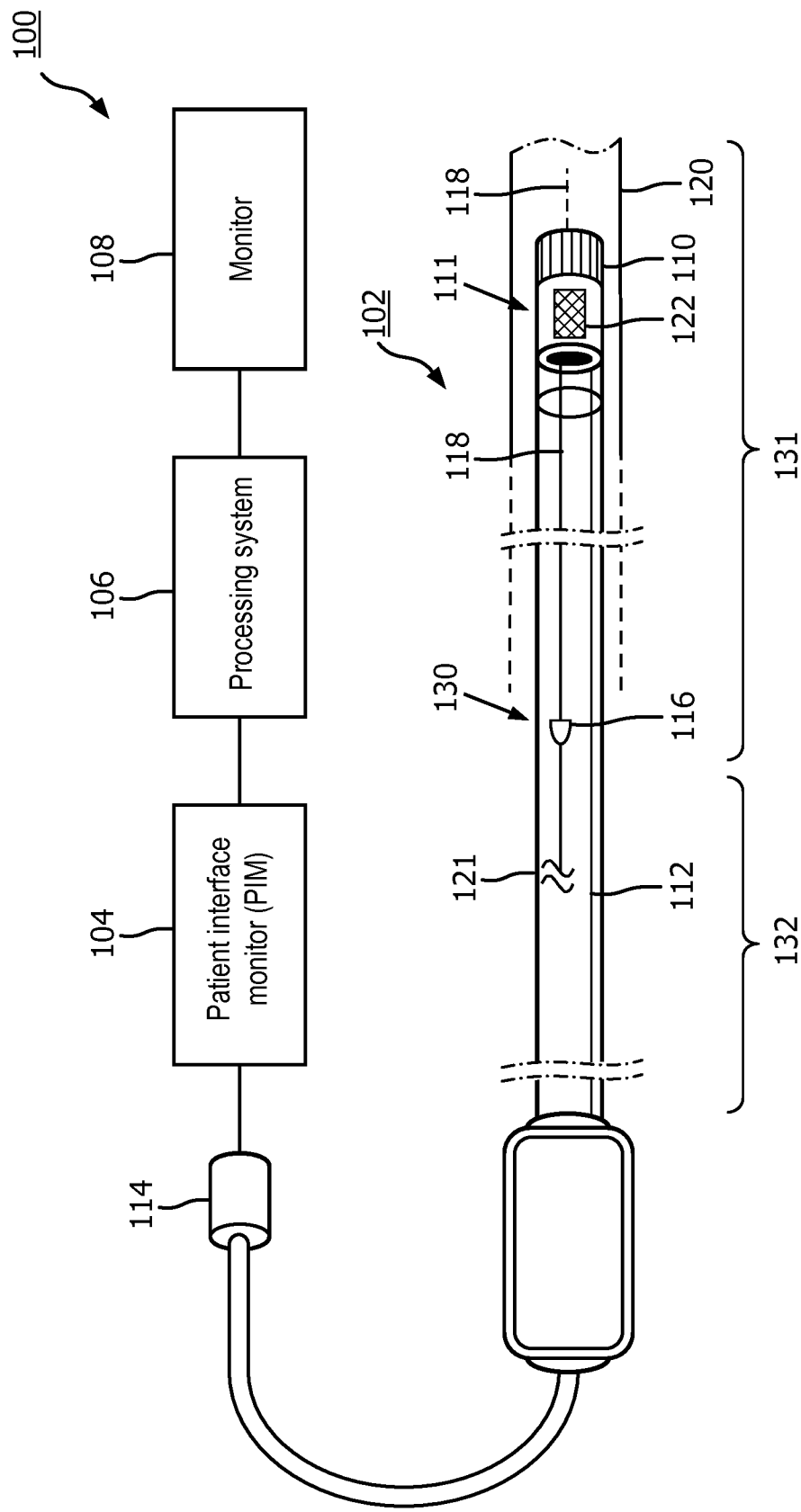
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. The intraluminal imaging system 100 may include an intraluminal imaging device 102, a patient interface module (PIM) 104, a processing system 106, and a monitor 108.

In some embodiments, the intraluminal imaging device 102 may comprise an ultrasound imaging device, e.g., an intravascular ultrasound (IVUS) imaging device, sized and shaped to be positioned within an anatomy of a patient. In that regard, the intraluminal imaging device 102 may obtain ultrasound imaging data from within the patient's anatomy. Generally, the intraluminal imaging device 102 may comprise a catheter, a guide wire, guide catheter, or combinations thereof. The intraluminal imaging device 102 may comprise a flexible elongate member 121. As used herein, "elongate member" or "flexible elongate member" includes at least any thin, long, flexible structure structurally arranged (e.g., sized and/or shaped) to be positioned within a lumen (or body lumen) of a patient's anatomy. As shown in FIG. 1, the intraluminal imaging device 102 is positioned within a body lumen 120. In some cases, the body lumen 120 is a blood vessel. In some embodiments, the flexible elongate member 121 may include one or more layers of braided metallic and/or polymer strands and/or a flexible hypotube. The braided layer(s) can be tightly or loosely braided in any suitable configuration, including any suitable per in count (pic). In some embodiments, the flexible elongate member 121 can include one or more metallic and/or polymer coils. All or a portion of the flexible elongate member 121 may have any suitable geometric cross-sectional profile (e.g., circular, oval, rectangular, square, elliptical, etc.) or non-geometric cross-sectional profile. For example, the flexible elongate member 121 can have a generally cylindrical profile with a circular cross-sectional profile that defines an outer diameter of the flexible elongate member 121. For example, the outer diameter of the flexible elongate member 121 can be any suitable value for positioning within a patient's anatomy, including between approximately 1 French (Fr) and approximately 15 Fr, including values such as 1 Fr, 2 Fr, 2.4 Fr, 2.5 Fr, 3 Fr, 3.5 Fr, 5 Fr, 7 Fr, 8.2 Fr, 9 Fr, and/or other suitable values both larger and smaller. In that regard, the intraluminal imaging device 102 may have an outer diameter less than 3 Fr. In particular, the intraluminal imaging device 102 may have an outer diameter of 0.014 inches, and outer diameter of 0.016 inches, or an outer diameter in therebetween.

The intraluminal imaging device 102 may include one or more lumens extending along all or a portion of the length of the flexible elongate member 121. Said lumens may be sized and shaped to receive and/or guide one or more diagnostic or therapeutic instruments through the patient's anatomy. In that regard, FIG. 1 illustrates guidewire 118 extending through a lumen of the intraluminal imaging device 102 between an exit/entry port 116 and a distal end of the intraluminal imaging device 102. The exit/entry port 116 is disposed near a junction 130 at which a distal portion 131 is coupled to a proximal portion 132. Accordingly, in some instances the intraluminal imaging device 102 may be a rapid-exchange catheter.

The intraluminal imaging device 102 may include an imaging assembly 111 mounted at the distal portion 131 near a distal end of the intraluminal imaging device 102. The imaging assembly 111 can include a transducer array 110 comprising a plurality of transducer elements. The intraluminal imaging device 102 may emit ultrasonic energy from the transducer array 110. The ultrasonic energy is reflected by tissue structures, e.g., walls of body lumen 120, surrounding the transducer array 110, and the ultrasound echo signals are received by the transducer array 110. The transducer array 110 can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The transducer array 110 may be a phased array. The transducer array 110 may be divided into segments, e.g., one or more rows and/or columns, that may be independently controlled and activated. The transducer array 110 and/or individual transducers may be arranged to emit and/or receive ultrasonic energy at an oblique angle relative to a longitudinal axis of the intraluminal imaging device 102.

The transducers of the transducer array 110 can be piezoelectric micromachined ultrasound transducers (PMUT), capacitive micromachined ultrasonic transducers (CMUT), single crystal, lead zirconate titanate (PZT), PZT composite, other suitable transducer types, and/or combinations thereof. Exemplary capacitive micromachined ultrasound transducers (cMUTs) are disclosed, for example, in U.S. application Ser. No. 14/812,792, filed Jul. 29, 2015, and titled "Intravascular Ultrasound Imaging Apparatus, Interface Architecture, and Method of Manufacturing," which is hereby incorporated by reference in its entirety. Depending on the transducer material, the manufacturing process for the transducer(s) can include dicing, kerfing, grinding, sputtering, wafer technologies (e.g., SMA, sacrificial layer deposition), other suitable processes, and/or combinations thereof.

For diagnosis and/or imaging, the center frequency of the transducer array 110 can be between 10 MHz and 70 MHz, for example, including values such as 10 MHz, 20 MHz, 30 MHz, 40 MHz, 45 MHz, 60 MHz, and/or other suitable values both larger and smaller. For example, lower frequencies (e.g., 10 MHz, 20 MHz) can advantageously penetrate further into the body lumen 120 and surrounding anatomy, such that more of a patient's anatomy is visible in the ultrasound images. Higher frequencies (e.g., 45 MHz, 60 MHz) can be better suited to generate more detailed ultrasound images of the patient's anatomy and/or fluid within the body lumen 120. In some embodiments, the frequency of the ultrasonic energy emitted by the transducer array 110 is tunable. In some instances, the transducer array 110 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the transducer array 110.

The imaging assembly 111 can further include one or more control circuits 122. In various contexts, control circuits 122 may be controllers, control chips, application specific integrated circuits (ASIC), or combinations thereof. Control circuits 122 may be configured to select particular transducer elements to be used for transmission/reception of ultrasonic energy, to provide transmission trigger signals to activate transmitter circuitry to generate an electrical pulse to excite the selected transducer elements, and/or to accept amplified echo signals received from the selected transducer elements. Multiple control circuit 122 configurations with various numbers of master circuits and slave circuits can be used to create a single ultrasound wave or multi-firing ultrasound wave device.

Figure 2:
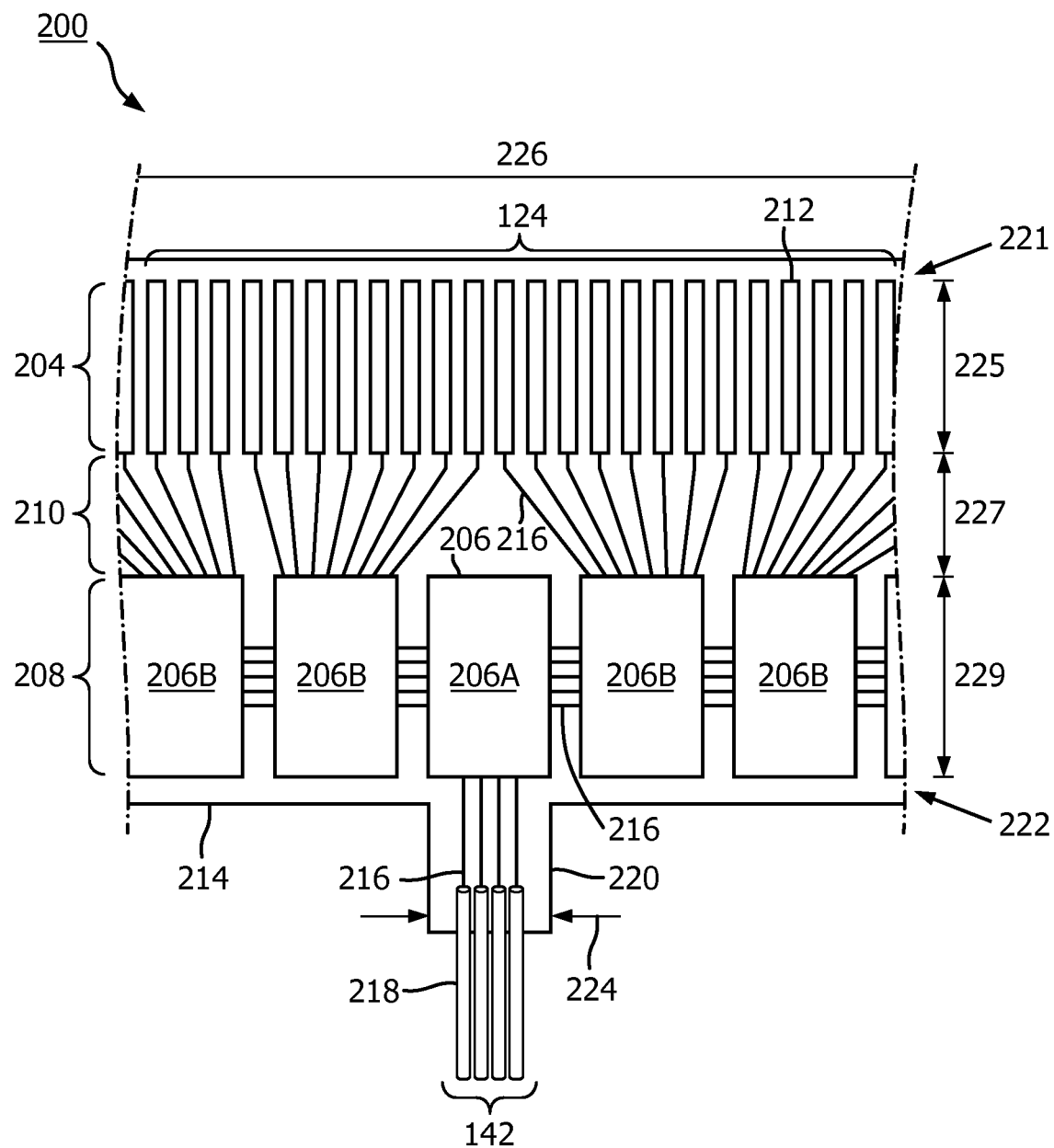
FIG. 2 is a diagrammatic top view of a portion of a flexible assembly in a flat configuration, according to aspects of the present disclosure.

The intraluminal imaging device 102 may include one or more electrical conductors 112 extending from the proximal portion 132 to the distal portion 131. The electrical conductor 112 is a transmission line bundle including a plurality of conductors, including one, two, three, four, five, six, seven, eight, or more conductors 218 (FIG. 2). It is understood that any suitable gauge wire can be used for the conductors 218. In an embodiment, the electrical conductor 112 can include a four-conductor transmission line arrangement with, e.g., 41 American wire gauge (AWG) wires. In an embodiment, the electrical conductor 112 can include an eight-conductor transmission line arrangement utilizing, e.g., 44 AWG wires. In some embodiments, 43 AWG wires can be used. The electrical conductors 112 may carry electrical signals between the PIM 104 and/or the processing system 106 and the imaging assembly 111. The electrical conductor 112 may terminate in a PIM connector 114. The PIM connector 114 may electrically couple the electrical conductor 112 to the PIM 104 and may further physically couple the intraluminal imaging device 102 to the PIM 104.

The PIM 104 may transfer received echo signals to the processing system 106 where an ultrasound image (including, in some cases, flow information) may be reconstructed and displayed on the monitor 108. In that regard, the PIM 104 facilitates communication of signals between the processing system 106 and the transducer array 110. This communication of signals may include the steps of: (1) providing commands to control circuits 122 to select the particular transducer element to be used to transmit and receive ultrasonic energy, (2) providing the transmit trigger signals to the control circuits 122 to activate the transmitter circuitry to generate an electrical pulse to excite the selected transducer elements, and/or (3) accepting amplified echo signals received from the selected transducer array elements via amplifiers included on the control circuits 122. In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage direct current (DC) power to support operation of the intraluminal imaging device 102, including circuitry within the transducer array 110.

The intraluminal imaging device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves, chambers, or other parts of the heart, and/or other systems of the body. In addition to natural structures, the intraluminal imaging device 102 may be used to examine man-made structures such as, but without limitation, heart valves, stents, shunts, filters and other devices.

In various embodiments, the intraluminal imaging device 102 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), forward-looking ICE (FLICE), transesophageal echocardiography (TEE), and/or other suitable imaging modalities. The intraluminal imaging device may also be configured to obtain physiologic data associated with pressure, flow, temperature, a fractional flow reserve (FFR) determination, a functional measurement determination, a coronary flow reserve (CFR) determination, optical coherence tomography (OCT), computed tomography, intravascular palpography, and/or other types of physiologic data. In some embodiments, the intraluminal imaging device 102 includes one or more features similar to traditional solid-state IVUS catheters, such as the EagleEye® catheter available from Volcano Corporation and those disclosed in U.S. Pat. No. 7,846,101 hereby incorporated by reference in its entirety.

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducers 212. The transducer control logic dies 206 are mounted on a flexible substrate 214 into which ultrasound transducers 212 have been previously integrated. The flexible assembly 200 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries), and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 200. In some embodiments, the film layer is between 5 μm and 100 μm, with some particular embodiments being between 5 μm and 25.1 μm, e.g., 6 μm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar, or the length 227 of the transition region 210 may be less than lengths 225 and 229, the length 227 of the transition region 210 can be greater than lengths 225 and 229 of the transducer region 204 and control region 208, respectively.

The control logic dies 206 are not necessarily homogenous. In some embodiments, a single controller is designated a master control logic die 206A and contains the communication interface for cable 142 which may serve as an electrical conductor, e.g., electrical conductor 112 (FIG. 1), between a processing system, e.g., processing system 106 (FIG. 1), and the flexible assembly 200. Accordingly, the master control circuit may include control logic that decodes control signals received over the cable 142, transmits control responses over the cable 142, amplifies echo signals, and/or transmits the echo signals over the cable 142. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed on the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 142 when the conductors 218 of the cable 142 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 µm. For example, in an embodiment, 5 µm conductive traces 216 are separated by 5 µm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 142 are coupled to the flexible substrate 214. For example, the bare conductors of the cable 142 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, control region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
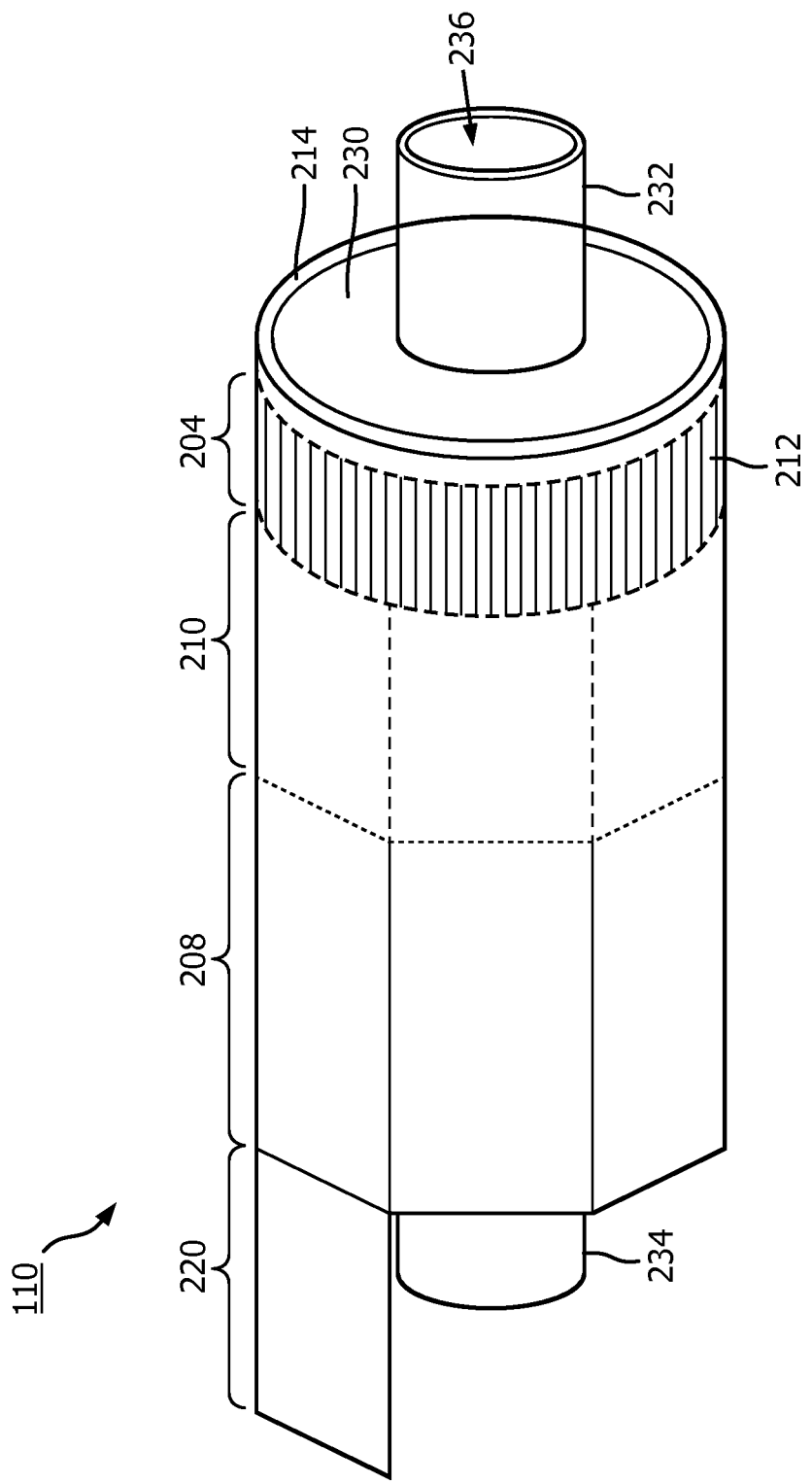
FIG. 3 is a diagrammatic side view of an imaging assembly, including a transducer array in a rolled configuration around a support member, according to aspects of the present disclosure.

FIG. 3 illustrates a rolled configuration of the flexible substrate 214. In some instances, the flexible assembly 200 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety. FIG. 3 is a diagrammatic perspective view with the flexible substrate 214 in the rolled configuration around a support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be a ferrule having a distal portion including a distal flange 232 and a proximal portion including a proximal flange 234. The support member 230 can be tubular in shape and define a lumen 236 extending longitudinally therethrough. The lumen 236 can be sized and shaped to receive the guide wire 118 (FIG. 1). The support member 230 can be manufactured using any suitable process. For example, the support member 230 can be machined and/or electrochemical machined or laser milled, such as by removing material from a blank to shape the support member 230, or molded, such as by an injection molding process.

Figure 4:
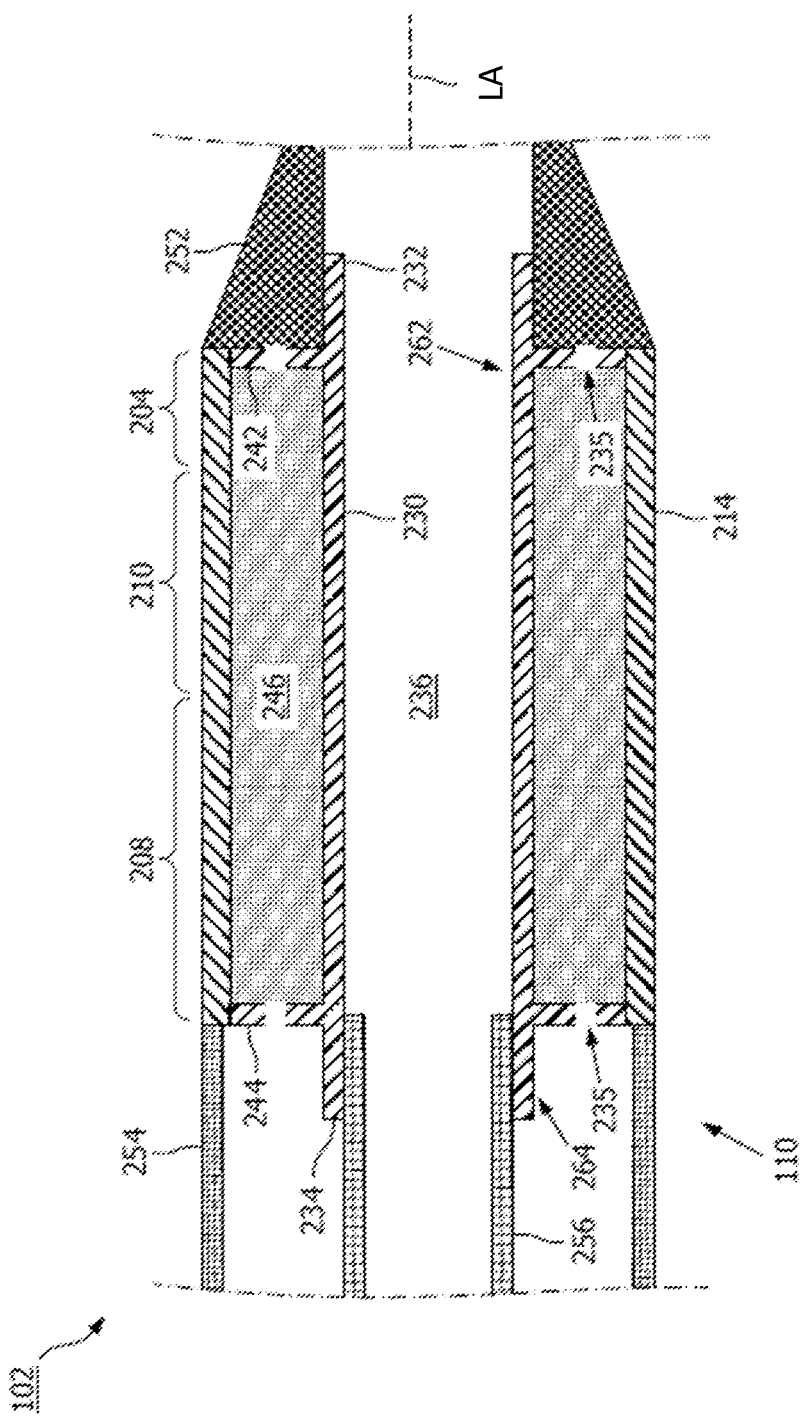
FIG. 4 is a diagrammatic cross-sectional side view of a distal portion of an intraluminal imaging device, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1). The support member 230 can be manufactured according to any suitable process. For example, the support member 230 can be machined and/or electrochemical machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion 204 (or transducer region 204), can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can be part of the flexible elongate member 121 (FIG. 1). The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive.

Figure 5A:
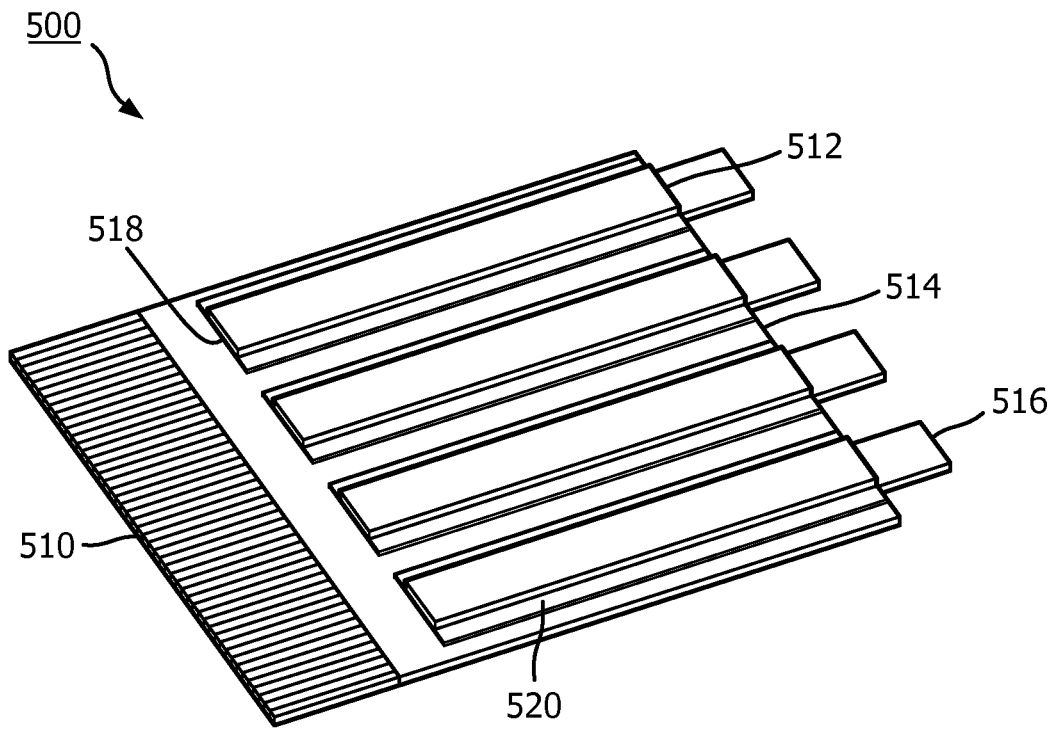
FIG. 5A is a diagrammatic perspective view of a flexible assembly with control chips, according to aspects of the present disclosure.

Turning now to FIG. 5A, a flexible assembly 500 is described. The flexible assembly 500 may make up a portion of an imaging assembly of an intraluminal imaging device. As the term is used herein, an imaging assembly may comprise a flexible assembly wrapped around a support member. Though not shown in FIG. 5A, the flexible assembly 500 may comprise a conductor providing for the transmission of electrical signals between the flexible assembly 500 and one or more elements of an intraluminal imaging system, e.g., a PIM or image processing system. Though illustrated in a flat state in FIG. 5A, the flexible assembly 500 may be configured to be wrapped around a support member one, two, three, four, or more times. In that regard, the flexible assembly 500 may comprise a transducer array 510 integrated in a flexible substrate 514 and a plurality of control circuits 512 disposed on the flexible substrate 514.

The transducer array 510 and plurality of control circuits 512 are spaced apart longitudinally from each other and may in some circumstances be referred to as being in-line. Spacing the transducer array 510 and control circuits 512 apart longitudinally may reduce the proportion of an outer diameter, e.g., of an intraluminal imaging device, attributable to said elements advantageously leaving more room for acoustic backing material which may improve the imaging performance of the transducer array 510. For example, the acoustic backing material may be insulating in nature and may prevent both ultrasonic energy being transmitted toward an interior of the intraluminal imaging device and may absorb any echoes returning from the interior.

Figure 5B:
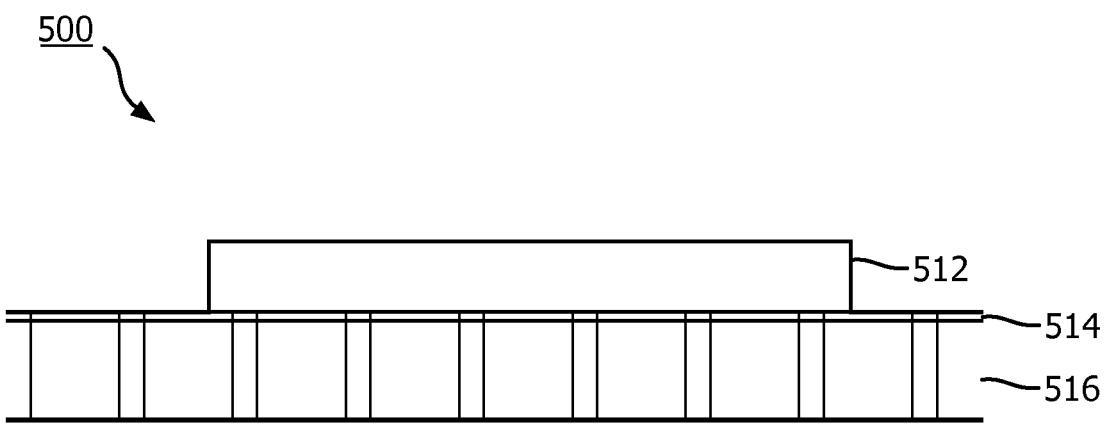
FIG. 5B is a diagrammatic frontal view of a flexible assembly with control chips, according to aspects of the present disclosure.

As similarly described above, the flexible substrate 514 may comprise one or more electrical traces providing for the transmission of electrical signals between the transducer array 510 and the plurality of control circuits 512. The flexible substrate 514 may itself be disposed on a base substrate 516. Some portions of the flexible substrate 514 can be disposed on the base substrate 516, while other portions only include the flexible substrate 514. The portions including only the flexible substrate 514 may have relatively more flexibility in some embodiments. In that regard, the flexible substrate 514 may be disposed between the base substrate 516 and one or more of the transducer array 510 and/or the control circuits 512. For example, FIG. 5B shows the flexible substrate 514 disposed between one of the control circuits 512 and the base substrate 516. The base substrate 516 may comprise silicon and may be flexible. In some cases, the base substrate 516 may not be a unitary structure but may be instead two or more separate pieces. For example, the base substrate 516 may comprise a series of strips.

The transducer array 510 may comprise a plurality of CMUT transducer elements which may be formed using wafer processing techniques. As similarly described above, the transducer array 510 may be a phased array and may be under the influence of the control circuits 512. For example, the control circuits 512 may send electrical signals to the transducer array and thereby trigger the emission of ultrasonic pulses from the transducer array. In some cases, individual control circuits 512 may control individual sections of the transducer array 510. Control circuits 512 may be soldered onto the flexible substrate 514 and/or onto the base substrate 516. In some cases, formation of the flexible assembly 500 is a wafer level process. The transducer array 510 may be processed onto a base substrate, e.g., silicon wafer. After the transducer array 510 is processed onto the base substrate, the base substrate may be provided with a polyimide layer, a metal interconnect layer, and a second polyimide layer and patterned into a desired shape. Then the base substrate is etched away from the backside to define base substrate islands. The interconnect areas between the base substrate islands may be flexible as the base substrate has been etched way leaving only the polyimide and interconnect behind.

The flexible assembly 500 may comprise a plurality of depressible regions 520 in which the control circuits 512 are located. When the flexible assembly 500 is wrapped around a support member, the depressible regions 520 may advantageously allow the control circuits 512 to be depressed toward the support member thereby reducing an outer profile or outer diameter of the control circuits 512. Depression of the control circuits 512 toward the support member advantageously reduces the outer profile of the control circuits 512. In that regard, the outer profile of the control circuits 512 may be reduced to such a degree that the outer profile of the control circuits 512 does not extend beyond an outer profile of the transducer array 510.

In some cases, the depressible regions 520 are regions of the flexible substrate 514. In other cases, the depressible regions 520 are distinct from the flexible substrate 514. The depressible regions 520 may be areas of increased flexibility within the flexible assembly 500. In that regard, the depressible regions 520 may be more flexible than other regions of the flexible substrate 514 and/or base substrate 516. In an embodiment, the depressible regions 520 may include one or more areas of reduced thickness relative to other regions of the flexible assembly 500. For example, the borders of the depressible regions 520 may be only one layer thick, e.g., may include only the flexible substrate 514, while other regions of the flexible assembly 500 include two or more layers, e.g., the flexible substrate 514 plus one or more of the base substrate 516, the transducer array 510, or the control circuits 512.

The flexible substrate 514 may include a plurality of slits 518. The slits 518 may be disposed at a distal end of the depressible regions 520. In that regard, the number of slits 518 may correspond to the number of depressible regions 520. The slits 518 may contribute to the ability of the depressible regions 520 to be depressed and/or to remain depressed. In some cases, the depressible regions 520 may be unable to be depressed without slits 518. The slits 518 may reduce the elasticity of the depressible regions 520. In other words, the slits 518 may reduce the tendency of the depressible regions 520 to return to their original position after being depressed. Accordingly, the slits 518 may advantageously enable the control regions or control circuits 512 to be depressed toward a support member and advantageously allow the control regions or control circuits 512 to retain their reduced outer profile once they have been depressed toward the support member.

Figure 6B:
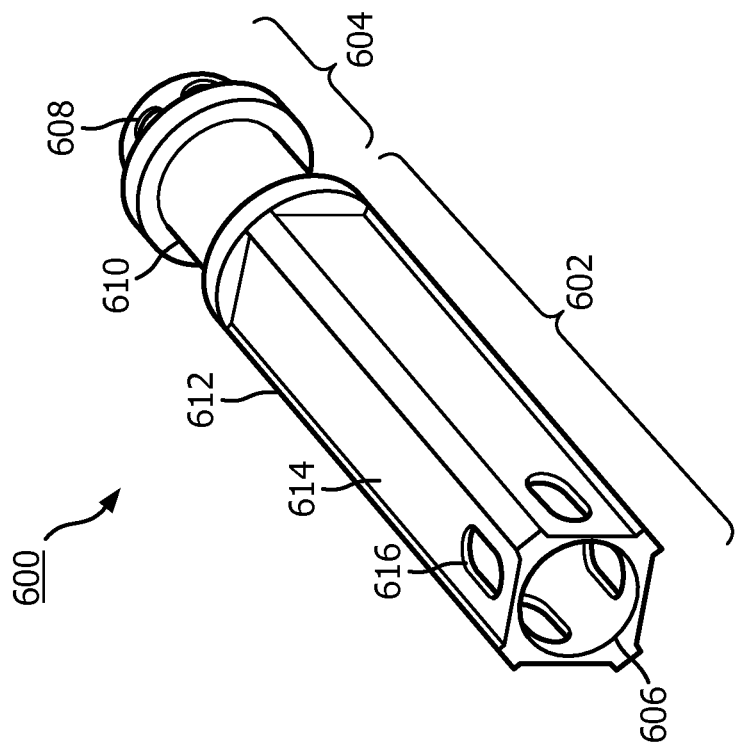
FIG. 6B is a diagrammatic perspective view of a support member, according to aspects of the present disclosure.
Figure 6A:
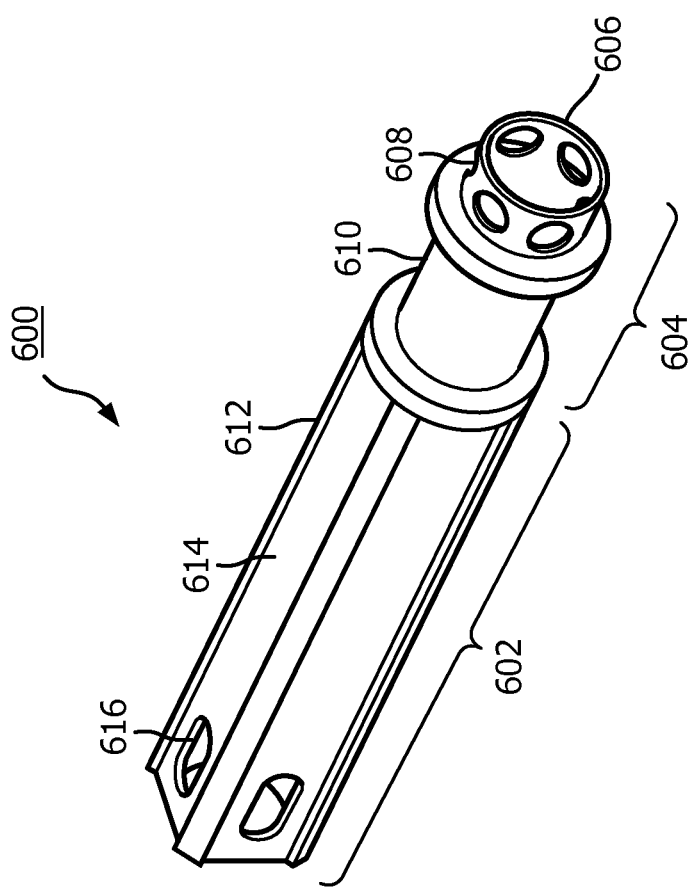
FIG. 6A is a diagrammatic perspective view of a support member, according to aspects of the present disclosure.

Turning now to FIGS. 6A and 6B, a support member 600 is described. The support member 600 may have a proximal region 602 and a distal region 604 as well as a lumen 606 extending therethrough. The support member 600 may be made of stainless steel or another suitable material and may shield a transducer array from electrical impulses emanating from a guide wire or other tool extending through the lumen 606. The support member 600 may reinforce an imaging assembly of an intraluminal imaging device, e.g., by supporting a flexible assembly. In that regard, the support member 600 may be sized and shaped to receive a flexible assembly, e.g., flexible assembly 500 (FIGS. 5A-5B), wrapped therearound.

The distal region 604 of the support member 600 may comprise one or more apertures 608. The apertures 608 may be disposed about the lumen 606 extending through the support member 600 from a proximal end to a distal end. In some cases, the apertures 608 may facilitate attachment of one or more elements of an intraluminal imaging device to the support member 600. For example, a distal tip element of an intraluminal imaging device may be anchored to the apertures 608. The apertures 608 may be circular, ovular, elliptical, square, rectangular, triangular, some other shape, or combinations thereof. The distal region 604 of the support member 600 may additionally comprise a spool 610. The spool 610 may be sized and shaped to receive a transducer array of a flexible assembly wrapped therearound. A cylindrical, central area of the spool 610 may be bounded on each end by circular rims of increased diameter. In that regard, a transducer array may be wrapped around and supported by the circular rims while resultant empty space between the cylindrical, central area is filled with acoustic backing material configured to acoustically insulate the transducer array from echoes coming from the center of an intraluminal imaging device in which the transducer array is implemented.

The proximal region 602 of the support member 600 may comprise one or more apertures 616. The apertures 616 may be disposed about the lumen 606 and may facilitate attachment of one or more elements of an intraluminal imaging device to the support member 600. For example, a flexible elongate member of an intraluminal imaging device may be anchored to the apertures 616. The apertures 616 may be circular, ovular, elliptical, square, rectangular, triangular, some other shape, or combinations thereof. The proximal region 602 may be generally square in shape and may comprise a plurality of recesses 614, e.g., four recesses, sized and shaped to receive a control circuit therein. In that regard, control circuits may be depressed into the plurality of recesses 614 thereby reducing their outer profile. In an embodiment, the recesses 614 are structured so that an outer profile of control circuits depressed into the plurality of recesses 614 does not extend beyond that of a transducer array wrapped around the spool 610. The proximal region 602 may further include a plurality of ridges 612 separating the recesses 614 from each other and advantageously providing structural stability, e.g., against lateral forces, for control circuits depressed into recesses 614.

Figure 7A:
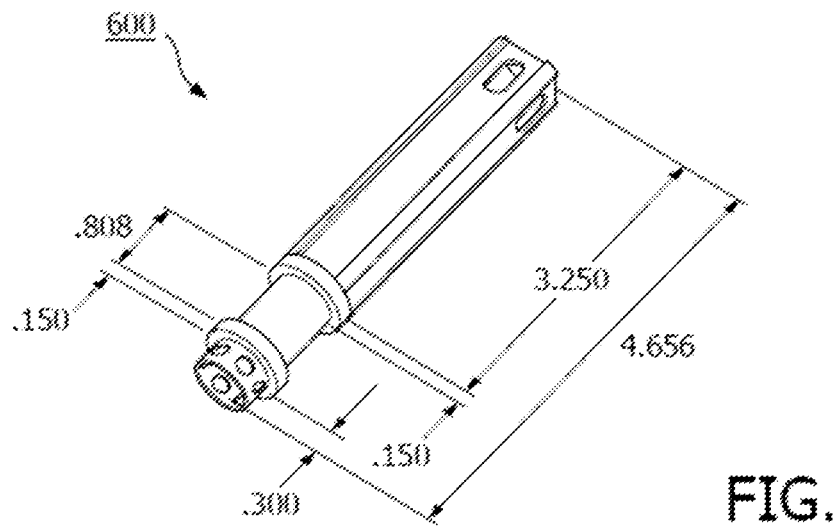
FIG. 7A is a diagrammatic perspective view of a support member, according to aspects of the present disclosure.
Figure 7B:
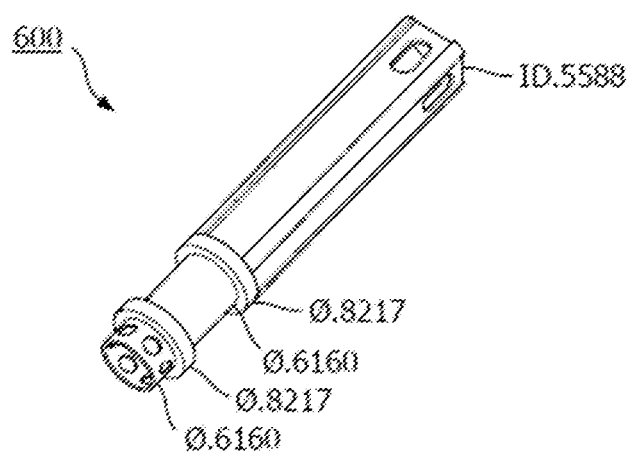
FIG. 7B is a diagrammatic perspective view of a support member, according to aspects of the present disclosure.
Figure 7C:
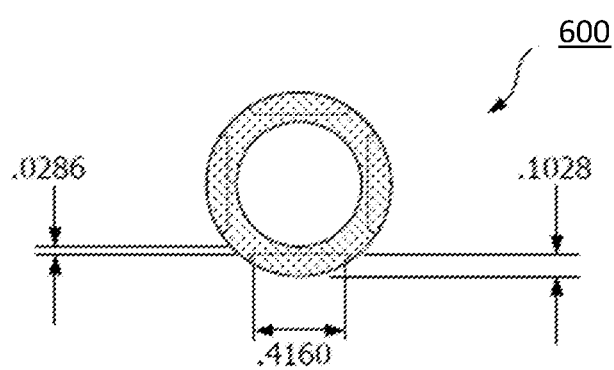
FIG. 7C is a diagrammatic cross-sectional view of a support member, according to aspects of the present disclosure.

FIGS. 7A-7C illustrate exemplary dimensions for the support member 600 measured in millimeters (mm). In that regard, FIG. 7A illustrates the length of various elements of the support member 600, FIG. 7B illustrates the diameter of various elements of the support member 600, and FIG. 7C is a cross-sectional view of the proximal end of the support member 600 and illustrates miscellaneous measurements of various elements of the support member 600.

Figure 8A:
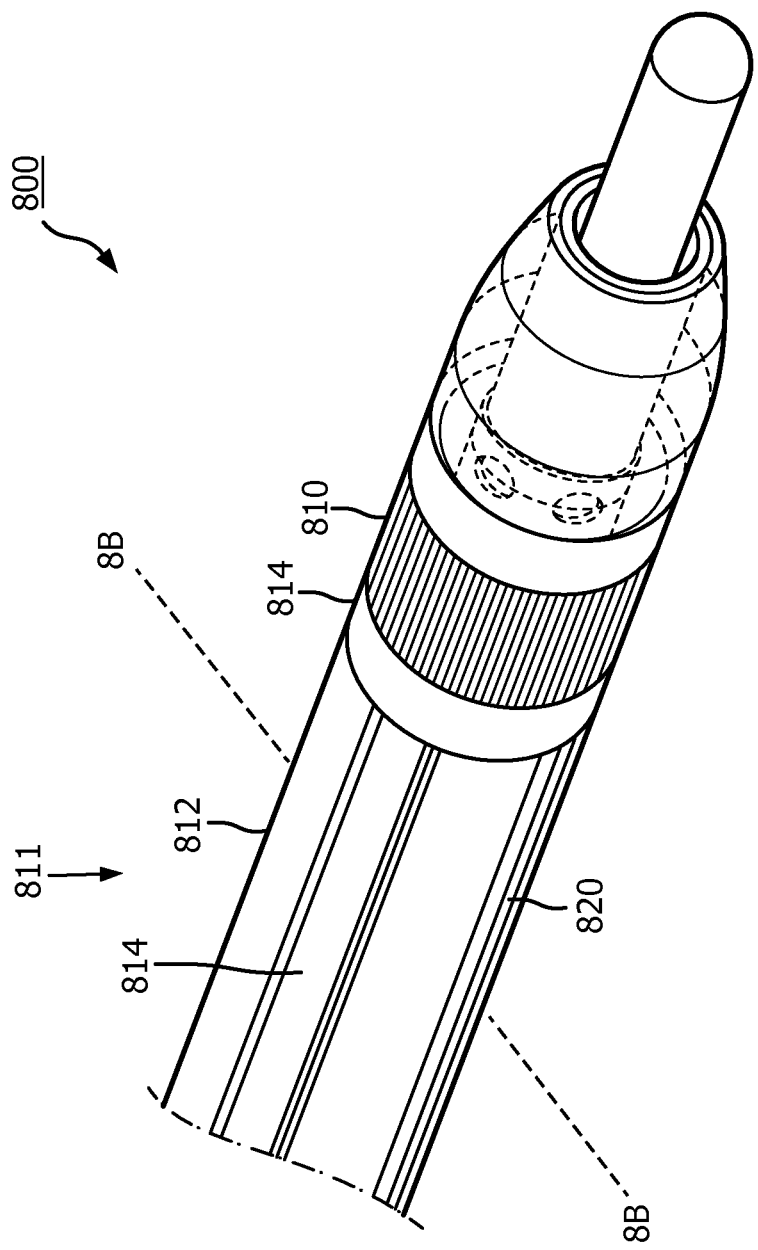
FIG. 8A is a diagrammatic perspective view of an intraluminal imaging device, according to aspects of the present disclosure.

Turning now to FIG. 8A, an intraluminal imaging device 800 is described. FIG. 8A illustrates a distal portion of the intraluminal imaging device 800. As similarly described above, the intraluminal imaging device 800 may be sized and shaped for introduction into a body lumen, e.g., a blood vessel, of a patient's anatomy and may be configured to perform one or more imaging operations including intravascular ultrasound (IVUS) imaging, forward looking intravascular ultrasound (FL-IVUS) imaging, intravascular photoacoustic (IVPA) imaging, intracardiac echocardiography (ICE), forward-looking ICE (FLICE), transesophageal echocardiography (TEE), and/or other suitable imaging modalities.

The intraluminal imaging device 800 may comprise an imaging assembly 811. The imaging assembly 811 may comprise a transducer array 810 integrated in a flexible substrate 814 and a plurality of control circuits 812 disposed on the flexible substrate 814. The imaging assembly 811 may further comprise a support member around which the flexible substrate 814 is wrapped. The transducer assembly 810 may be aligned or co-located longitudinally with a spool of the support member and the plurality of control circuits 812 may be aligned or co-located longitudinally with a plurality of recesses of the support member. In that regard, as similarly described above, the flexible substrate may include a plurality of depressible regions 820 in which the control circuits 812 are located. As shown in FIG. 8A, the plurality of control circuits 812 have been depressed into recesses of a support member around which the flexible substrate 814 is wrapped. In embodiments, a longitudinal length of the rigid portion of the device 800 can be between 4 mm and 5 mm, including values such as 4.3 mm, 4.4 mm, 5 mm, and/or other suitable values, both larger and smaller.

Figure 8B:
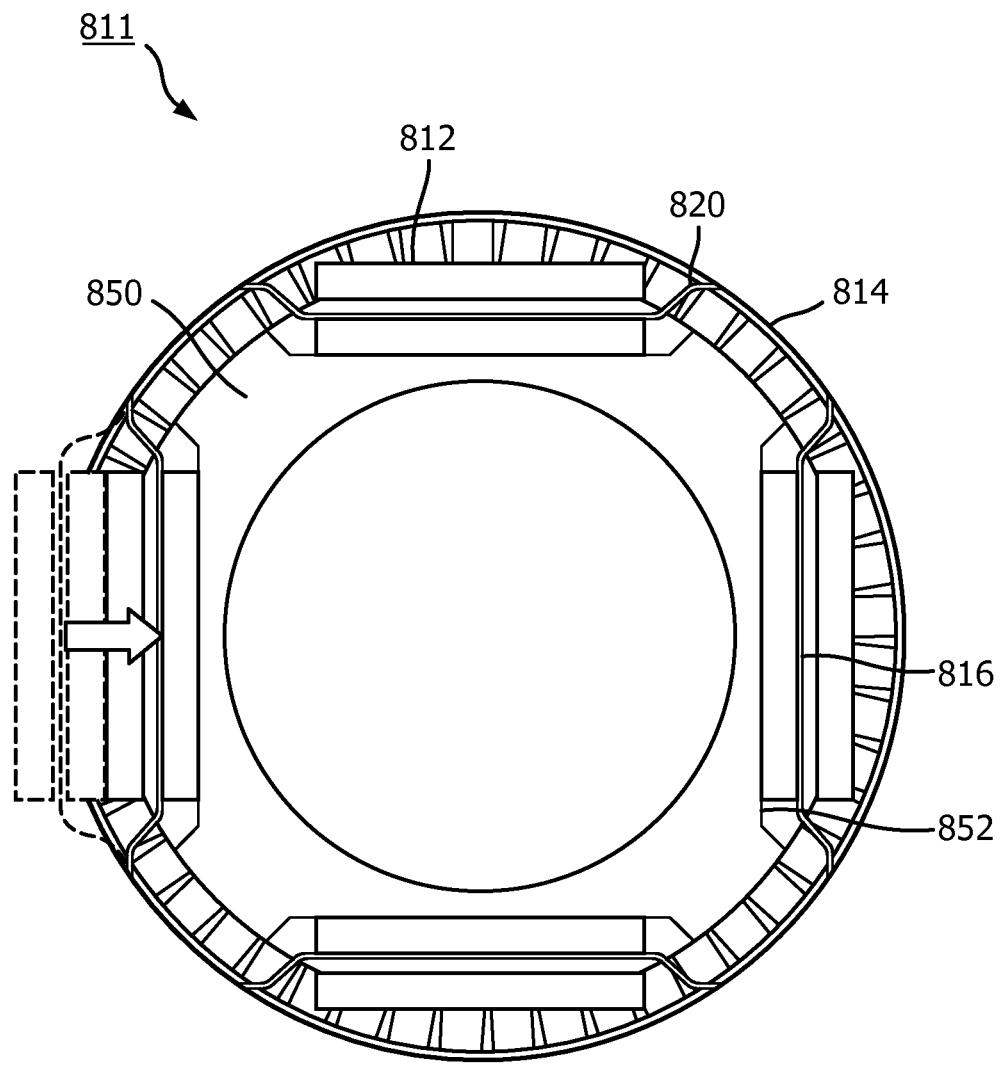
FIG. 8B is a diagrammatic cross-sectional view of an intraluminal imaging device at a control chip section, according to aspects of the present disclosure.

FIG. 8B provides a cross sectional view of the imaging assembly 811 taken along the line 8B illustrated in FIG. 8A. As shown, the control circuits 812 have been depressed into recesses 852 of support member 850. In that regard, the control circuits 812 have been depressed to such a degree that in each instance base substrate 816 is flush with the bottom of recess 852. FIG. 8B also illustrates a range of motion through which the control circuits 812 may move. In an undepressed state, the control circuits 812 may have an outer profile that extends beyond that of outer diameter of other elements of the imaging assembly 811, e.g., transducer array 810. Depressing the control circuits into the recesses 852 may reduce their outer profile such that it does not extend beyond that of other elements of the imaging assembly 811, e.g., transducer array 810.

Figure 8C:
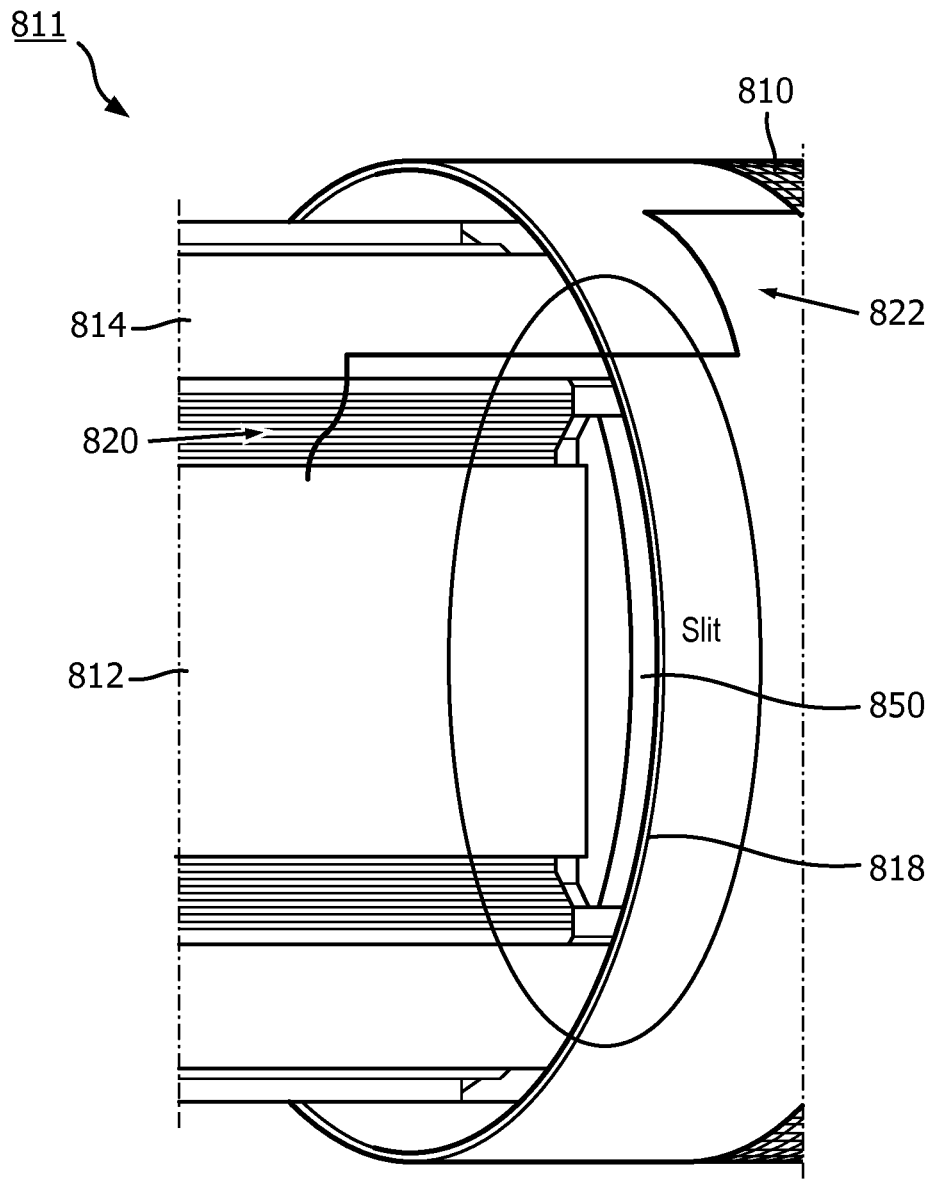
FIG. 8C is a diagrammatic perspective view of an intraluminal imaging device, according to aspects of the present disclosure.

FIG. 8C provides a perspective view of the imaging assembly 811 with the control circuits 812 depressed into recesses 852. FIG. 8C highlights the operation of slits 818 in facilitating depression of the control circuits 812 into recesses 852 of the support member 850. FIG. 8C also illustrates an exemplary path of an electrical trace 822. The electrical trace 822 may run from the control circuit 812 to the transducer array 810 and may conduct electrical signals therebetween. Though not shown in FIG. 8C, one or more electrical traces or other circuitry may extend laterally between control circuits 812 and may enable lateral communication between control circuits 812. In that regard, such an electrical trace may extend from a first control circuit 812, cross a first depressible region 820, cross a region of the flexible substrate 814, cross a second depressible region 820, and connect to a second control circuit 812. Lateral communication between control circuits 812 may advantageously improve the speed at which signals may be transmitted between the control circuits 812 and/or it may advantageously provide a bypass if other communication routes are damaged.

Figure 9:
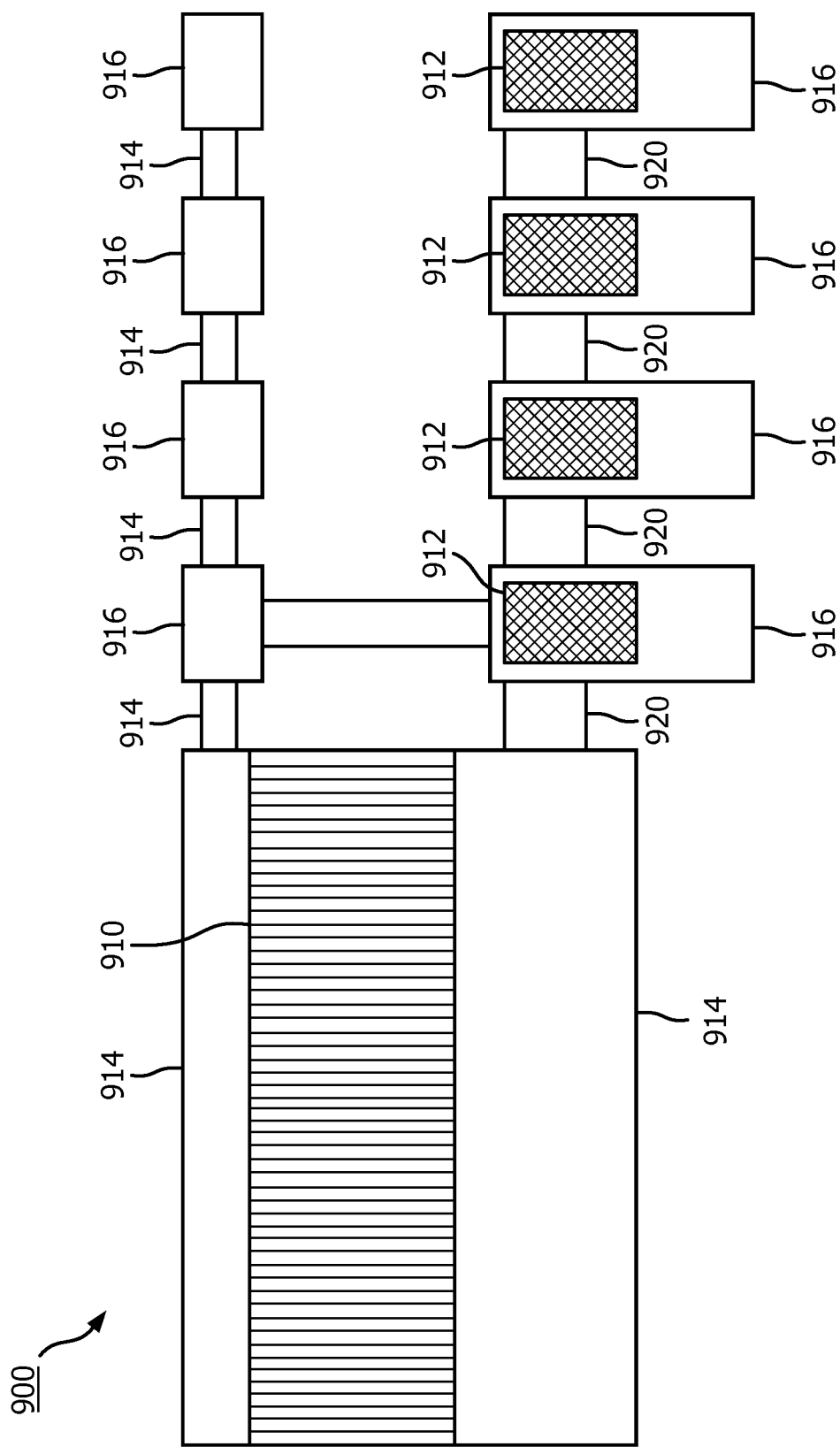
FIG. 9 is a diagrammatic top view of a flexible assembly, according to aspects of the present disclosure.

Turning now to FIG. 9, a flexible assembly 900 is described. The flexible assembly 900 may comprise a transducer array 910 integrated in a flexible substrate 914. The flexible assembly 900 may further comprise a plurality of control circuits 912 disposed on depressible regions 920, which may comprise regions of the flexible substrate 914, and which may themselves be disposed on a base substrate 916. The base substrate 916 may not be a single unit but may instead be divided into a plurality of islands. As similarly described above, the flexible assembly 900 may be configured to be wrapped around a support member. When wrapped around the support member, transducer array 910 may align longitudinally with a spool of the support member while control circuits 912 align longitudinally with a plurality of recesses sized and shaped to receive the control circuits 912 therein. In that regard, the depressible regions 920 may allow the control circuits 912 to be depressed into the plurality of recesses. In some cases, the relatively thin sections of material, e.g., depressible regions 920, connecting the control circuits 912 to each other may allow the control circuits 912 to be depressed deeper into recesses of a support member than would an embodiment featuring thicker sections of connecting material. Deeper depression into the recesses of the support member may further reduce the outer profile of the control circuits 912. In embodiments, a longitudinal length of the rigid portion of the device 900 can be between 4 mm and 5 mm, including values such as 4.3 mm, 4.4 mm, 5 mm, and/or other suitable values, both larger and smaller.

Figure 10:
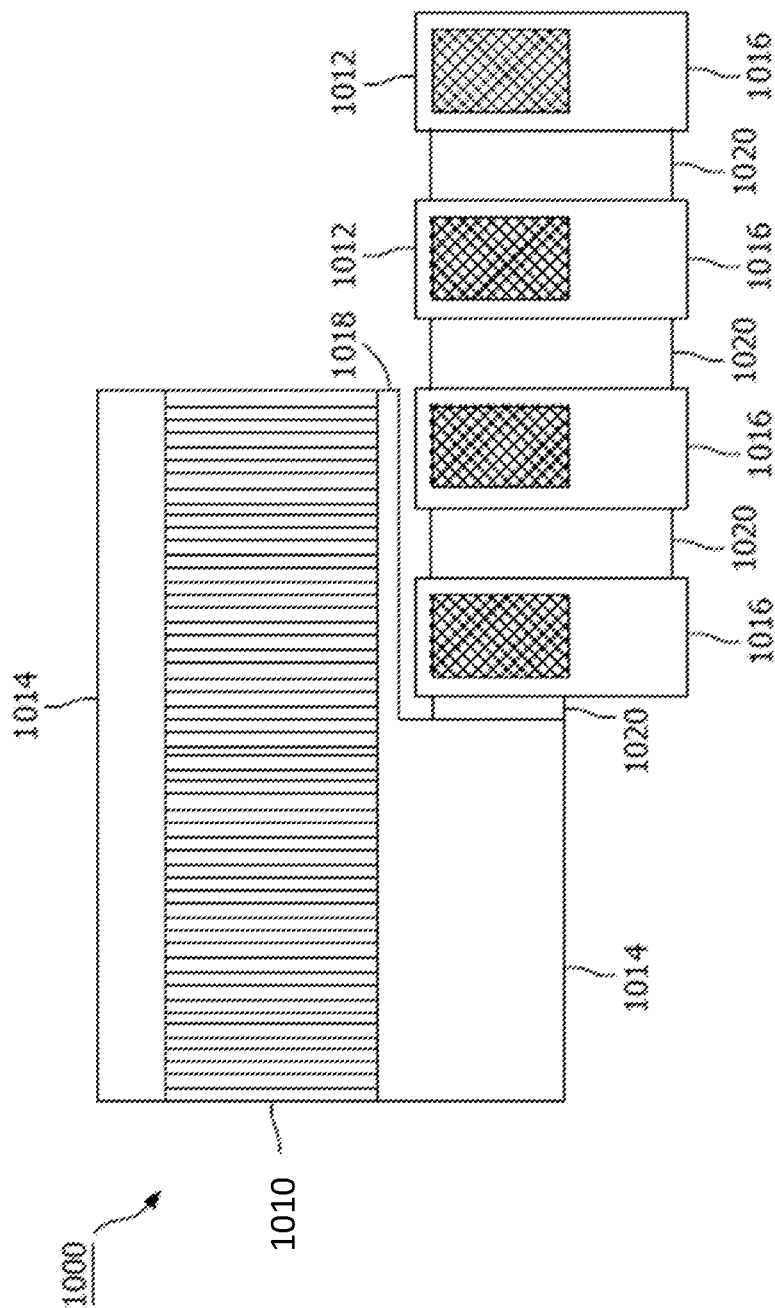
FIG. 10 is a diagrammatic top view of a flexible assembly, according to aspects of the present disclosure.

Turning now to FIG. 10, a flexible assembly 1000 is described. The flexible assembly 1000 may comprise a transducer array 1010 disposed on a flexible substrate 1014. The flexible assembly 1000 may further comprise a plurality of control circuits 1012 disposed on regions 1020, which may comprise regions of the flexible substrate 1014, and which may themselves be disposed on a base substrate 1016. The base substrate 1016 may not be a single unit but may instead be divided into a plurality of islands. As similarly described above, the flexible assembly 1000 may be configured to be wrapped around a support member. Regions 1020 may facilitate wrapping the flexible assembly 1000 around the support member. When wrapped around the support member, transducer array 1010 may align longitudinally with a spool of the support member while control circuits 1012 align longitudinally with a plurality of recesses sized and shaped to receive the control circuits 1012 therein. The flexible assembly 1000 may comprise a slit 1018 to facilitate the control circuits achieving a reduced outer profile, e.g., a smaller diameter, than the transducer array 1010 when the flexible assembly 1000 is wrapped around the support member.

Figure 11:
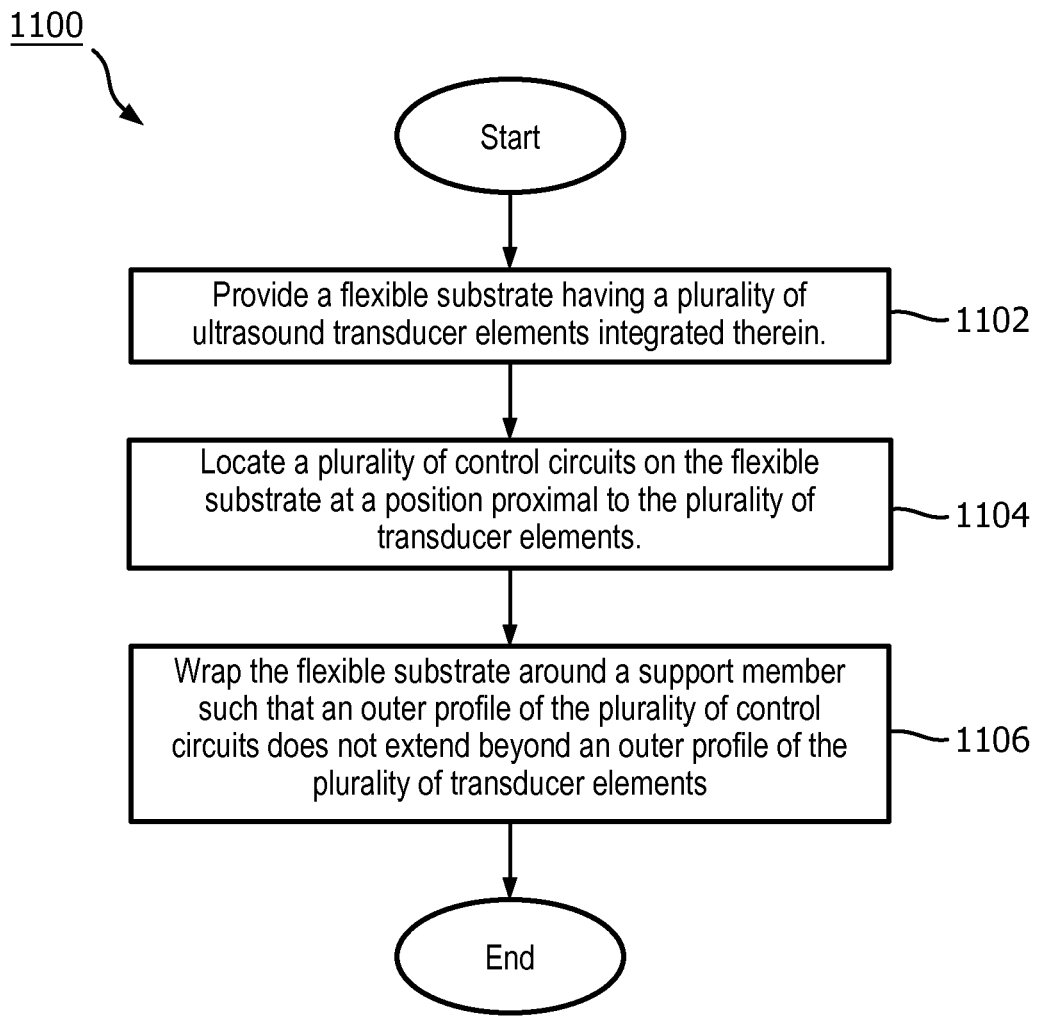
FIG. 11 is a flow chart of a method, according to aspects of the present disclosure.

Turning now to FIG. 11, a method 1100 is described. The method begins at block 1102 where a flexible substrate is provided that has a plurality of ultrasound transducer elements integrated therein. In some cases, the method may include formation of the flexible substrate with integrated ultrasound transducer elements. For example, the method may include one or more of providing a base substrate, e.g., silicon, processing the ultrasound transducer elements onto the base substrate, and forming the flexible substrate around the ultrasound transducer elements. The method may further include etching or defining the base substrate, e.g., using wafer processing techniques, into one or more base substrate islands. The flexible substrate may connect the one or more base substrate islands. The method continues at block 1104 where a plurality of control circuits is located on the flexible substrate at a position proximal to the plurality of transducer elements. In an embodiment, locating the plurality of control circuits on the flexible substrate comprises locating the plurality of control circuits on a depressible region of the flexible substrate. The flexible substrate is wrapped, at block 1106, around a support member such that an outer profile of the plurality of control circuits does not extend beyond an outer profile of the plurality of transducer elements. In an embodiment, wrapping the flexible substrate around the support member comprises wrapping the plurality of transducer elements around a spool of the support member. In an embodiment, the method further comprises depressing the plurality of control circuits into a plurality of recesses of the support member.

Figure 12:
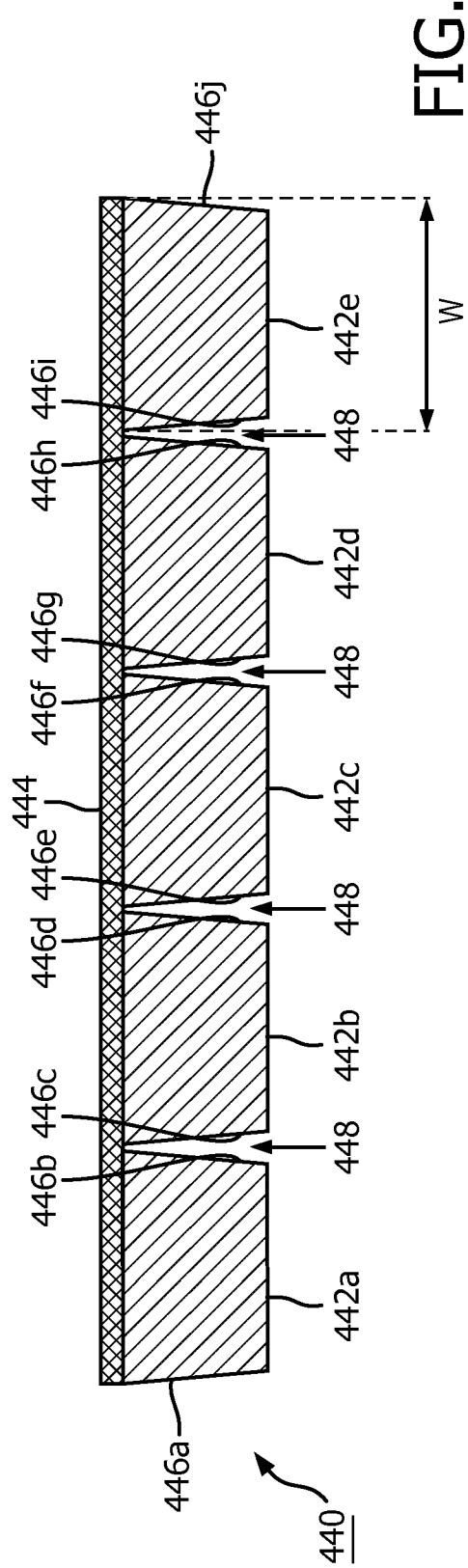
FIGS. 12 and 13 illustrate exemplary transducers arranged on an exemplary flexible substrate according to aspects of the present disclosure. In particular.
Figure 13:
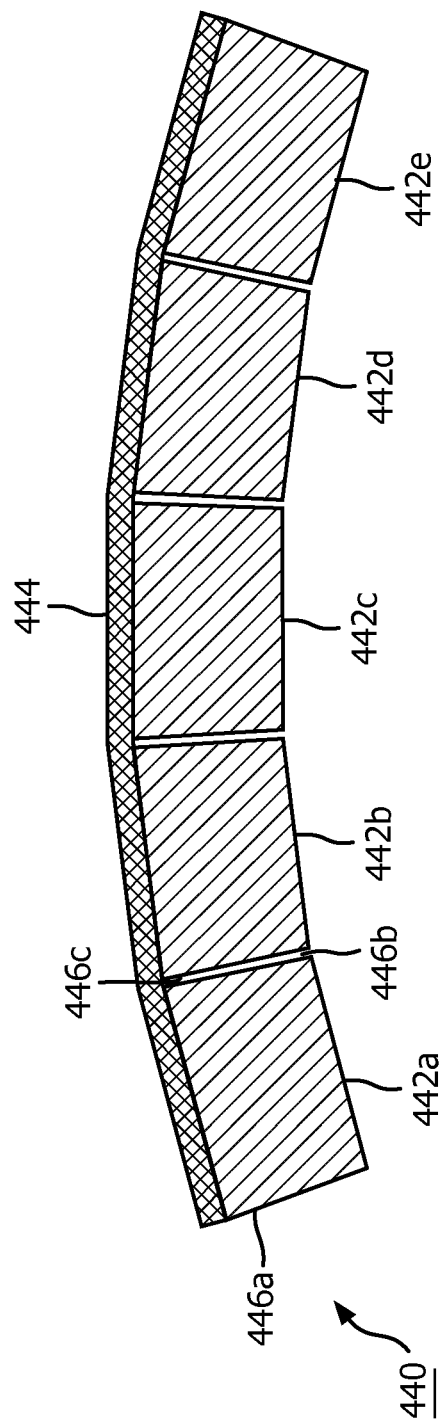

FIGS. 12 and 13 illustrate an array 440 of transducer elements 442 arranged on a substrate 444 according to aspects of the present disclosure. In particular, FIG. 12 is a diagrammatic side view of the array 440 of transducer elements 442a-e with the substrate 444 in a flat configuration, and FIG. 13 is a diagrammatic side view of the array 440 of transducer elements 442a-e with the substrate 444 in a curved (or rolled) configuration. As shown in FIG. 12, the transducer elements 442a-e are arranged linearly on the substrate 444. In some embodiments, the substrate 444 comprises a flexible substrate. The transducer elements 442 include a width W. The width W may range from 20 microns to 100 microns. For example, the width W may be 40 microns. The transducer elements 442a-e include angled sidewalls 446a-j. The sidewalls 446 are non-perpendicular to one another, thereby defining wedge-shaped trenches 448 between the non-perpendicular sidewalls 446 and facilitating bending of the acoustic section. In some examples, the sidewalls 446 can be angled approximately between 1° and 45°, between 1° and 30°, between 1° and 15°, between 1° and 10°, between 1° and 5°, including values such as 22.5°, 11.25°, 9°, 5.625°, 4.5°, 2.8125°, and/or other suitable values, both larger and smaller. The angle of the sidewalls 446 can be based on the number of transducer elements 442, the diameter of the scanner assembly 110, the diameter of the imaging device 102, the dimensions of the transducer elements 442, the spacing between adjacent transducer elements 442, etc. In some embodiments, the sidewalls 446 of all transducer elements can be angled by the same amount. In other embodiments, the sidewalls 446 of different transducers elements are angled by different amounts.

As shown in FIG. 13, when the substrate 444 is curved or flexed, the transducer elements 442 contact one another along the entire length of their sidewalls. For example, the sidewall 446b of the transducer element 442a comes into full contact with the sidewall 446c of the transducer element 442b. Thus, this non-perpendicular trench configuration maximizes the surface area available on the substrate for the transducer elements 442. Other non-perpendicular separations of the transducer elements 442 are contemplated. For example, in some embodiments, the sidewalls 446 may be curved or serpentine, where neighboring sidewalls 446 are configured to rest against one another or contact one another along at least a portion of the length of the trench 448 when the flexible substrate 444 is flexed or in a curved configuration. One method of manufacture may be anisotropic dry etching or an appropriate combination of anisotropic dry etching and isotropic dry etching, such that the desired trench sidewall profile is obtained.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
a flexible elongate member configured to be inserted into a body lumen of a patient, the flexible elongate member comprising a proximal portion and a distal portion; and
an ultrasound imaging assembly disposed at the distal portion of the flexible elongate member, the ultrasound imaging assembly comprising:
a support member different than, and coupled to the distal portion of, the flexible elongate member, wherein the support member comprises a central lumen extending longitudinally through an entire length of the support member; and
a flexible substrate positioned around the support member, wherein the flexible substrate comprises:
a plurality of ultrasound transducer elements;
a plurality of control circuits spaced from the plurality of ultrasound transducer elements in a longitudinal direction;
a plurality of slits extending in a lateral direction perpendicular to the longitudinal direction,
wherein the plurality of slits is configured to allow an arrangement of the plurality of control circuits relative to the plurality of ultrasound transducer elements, wherein the arrangement comprises the plurality of control circuits being disposed radially inward relative to the plurality of ultrasound transducer elements, and
wherein, in the longitudinal direction, the plurality of slits is positioned between the plurality of control circuits and the plurality of ultrasound transducer elements.

2. The intraluminal imaging device of claim 1, wherein the support member comprises a proximal portion and a distal portion, the proximal portion comprising a plurality of recesses each configured to receive a control circuit of the plurality of control circuits therein.

3. The intraluminal imaging device of claim 2, wherein the distal portion of the support member comprises a spool configured to receive the plurality of ultrasound transducer elements.

4. The intraluminal imaging device of claim 3, wherein the plurality of control circuits are longitudinally co-located with the plurality of recesses and the plurality of ultrasound transducer elements are longitudinally co-located with the spool.

5. The intraluminal imaging device of claim 2, wherein the proximal portion of the support member comprises four recesses.

6. The intraluminal imaging device of claim 1, wherein, in the longitudinal direction, the plurality of slits are positioned only distal to the plurality of control circuits.

7. The intraluminal imaging device of claim 1, wherein the flexible substrate includes circuitry enabling lateral communication between control circuits of the plurality of control circuits.

8. The intraluminal imaging device of claim 1, wherein the support member is made of at least one of stainless steel or a polymer.

9. The intraluminal imaging device of claim 1, wherein the plurality of ultrasound transducer elements comprises a plurality of capacitive micromachined ultrasound transducers.

10. The intraluminal imaging device of claim 1,
wherein the plurality of control circuits comprise a first outer profile,
wherein the plurality of ultrasound transducer elements comprise a second outer profile, and
wherein the first outer profile does not extend beyond the second outer profile.

11. The intraluminal imaging device of claim 1,
wherein the flexible substrate comprises a plurality of first regions and a plurality of second regions alternating with the plurality of first regions in the lateral direction,
wherein the plurality of control circuits are disposed on the plurality of first regions, wherein, in the lateral direction, the plurality of control circuits are spaced from one another by the plurality of second regions, and
wherein the plurality of first regions and the plurality of second regions define a continuous perimeter.

12. The intraluminal imaging device of claim 11,
wherein the flexible substrate further comprises a plurality of third regions, wherein the plurality of third regions are located on either side of each control circuit of the plurality of control circuits,
wherein a third region of the plurality of third regions extends radially inward from a second region of the plurality of second regions to a first region of the plurality of first regions.

13. The intraluminal imaging device of claim 1, wherein the slits of the plurality of slits extend completely through the flexible substrate in the lateral direction perpendicular to the longitudinal direction.

14. A method of assembling an intraluminal imaging device, the method comprising:
providing a flexible substrate comprising:
a plurality of ultrasound transducer elements;
a plurality of control circuits spaced from the plurality of ultrasound transducer elements in a longitudinal direction; and
a plurality of slits extending in a lateral direction perpendicular to the longitudinal direction; and positioning the flexible substrate around a support member, wherein the plurality of slits is configured to allow an arrangement of the plurality of control circuits relative to the plurality of ultrasound transducer elements, wherein the arrangement comprises the plurality of control circuits being disposed radially inward relative to the plurality of ultrasound transducer elements, wherein, in the longitudinal direction, the plurality of slits are positioned between the plurality of control circuits and the plurality of ultrasound transducer elements such that the plurality of control circuits is disposed radially inward relative to the plurality of ultrasound transducer elements, wherein the support member is different than, and coupled to a distal portion of, a flexible elongate member, and wherein the support member comprises a central lumen extending longitudinally through an entire length of the support member.

15. The method of claim 14, wherein the support member comprises a proximal portion and a distal portion, the proximal portion including a plurality of recesses each sized and shaped to receive a control circuit of the plurality of control circuits therein.

16. The method of claim 15, wherein the support member comprises four recesses.

17. The method of claim 15, wherein the distal portion of the support member includes a spool sized and shaped to receive the plurality of ultrasound transducer elements.

18. The method of claim 17, wherein the positioning the flexible substrate around the support member comprises wrapping the plurality of ultrasound transducer elements around the spool.

19. The method of claim 14, wherein, in the longitudinal direction, the plurality of slits are disposed only distal to the plurality of control circuits.

20. The method of claim 14, further comprising moving the plurality of control circuits radially inward.

21. The method of claim 14, wherein the flexible substrate includes circuitry enabling lateral communication between control circuits of the plurality of control circuits.

22. The method of claim 14, wherein the support member is made of at least one of stainless steel or a polymer.

* * * * *